United States Patent

Yates et al.

[11] Patent Number: 6,077,982
[45] Date of Patent: Jun. 20, 2000

[54] PURIFICATION OF 1,1,1,3,3-PENTAFLUOROPROPANE (R-245FA)

[75] Inventors: Stephen Frederic Yates; Romulus Gaita, both of Cook County, Ill.

[73] Assignee: Allied Signal Inc., Morristown, N.J.

[21] Appl. No.: 09/123,381

[22] Filed: Jul. 27, 1998

Related U.S. Application Data

[63] Continuation-in-part of application No. 08/628,064, Apr. 4, 1996, abandoned.

[51] Int. Cl.$^7$ .................................................. C07C 17/38
[52] U.S. Cl. ...................................... 570/177; 204/157.95
[58] Field of Search ........................ 570/177; 204/157.95

[56] References Cited

U.S. PATENT DOCUMENTS

| | | |
|---|---|---|
| 5,336,377 | 8/1994 | Yates . |
| 5,399,796 | 3/1995 | Correia . |

OTHER PUBLICATIONS

Fredericks et al., *J. Chem. Soc.* (1960) 144.
Galiba et al. *J. Chem. Soc.* (1964) 1321.
Migita et al. *Bull. Chem. Soc.* Japan 40 (1967) 920.
Zefirov et al. *Tetrahedron Letters*, vol. 24 No. 46 (1983) pp. 5133–5136.

*Primary Examiner*—Alan Siegel
*Attorney, Agent, or Firm*—Jay P. Friendenson; Marie L. Collazo

[57] ABSTRACT

In the synthesis of 1,1,1,3,3-pentafluoropropane (R-245fa), a mixture of R-245fa and the impurity 1-chloro-3,3,3-trifluoropropene (R-1233zd) is purified and R-1233zd is removed from the mixture by contacting the mixture with 1–5 mols of chlorine for each mol of R-1233zd in the presence of ultraviolet light having a wavelength between about 300 to 400 nm which provides at least 0.02 watts-hour/kg of the mixture, the R-1233zd being reduced to below 10 wt. ppm or lower, as it is converted to 1,2,2-trichloro-3,3,3-trifluoropropane (R-233) or other propane which contains more chlorine and which has a higher boiling point than R-245fa and can be separated easily from R-245fa, the photochlorination being effected in a manner such that at least about 96 wt. % of the starting amount of R-245fa is maintained in the mixture.

12 Claims, No Drawings

PURIFICATION OF 1,1,1,3,3-PENTAFLUOROPROPANE (R-245FA)

CROSS-REFERENCE TO RELATED APPLICATION

This application is a continuation-in-part of application Ser. No. 08/628,064, filed Apr. 4, 1996 now abandoned.

BACKGROUND OF THE INVENTION

This invention relates principally to the purification of 1,1,1,3,3-pentafluoropropane, also designated R-245fa, which has been of particular interest as a replacement for chlorofluorocarbons having similar physical properties, particularly R-113. R-245fa may be prepared by a three-step process involving reaction of carbon tetrachloride, CCl4, with vinylidene chloride, $CH_2=CCl_2$, reacting the product with HF to form $CF_3CH_2CF_2Cl$ (R-235fa) and finally, hydrogenation to remove the chlorine atom, as disclosed in pending U.S. application Ser. No. 08/099,676.

It is characteristic of such reactions that many by-products are formed, containing varying numbers of hydrogen, chlorine, and fluorine atoms on $C_1$-$C_3$ compounds. These by-products and the unreacted feed material may be separated by distillation where possible. Some compounds are relatively harmless since their presence does not greatly alter the physical properties for which R-245fa is useful. One by-product which must be removed because of its toxicity is 1-chloro-3,3,3,-trifluoropropene (R-1233zd), although only relatively small amounts are typically present in R-245fa as formed. R-1233zd has a boiling point close to that of R-245fa making them difficult to separate by distillation. After distillation of the crude product, R-1233zd will still be present in amounts from about 300 to 20,000 ppm (wt.). It should be reduced to below about 100 ppm (wt.) according to the specifications of the Panel for Advancement of Fluorocarbon Test (PAFTII). Preferably, the R-1233zd should be reduced to 20 ppm (wt.) and most preferably below about 10 ppm (wt.).

Further improvement in methods of purifying R-245fa, particularly with respect to eliminating R-1233zd, is desired and the present inventors have discovered a means for purification by photochlorination which will be disclosed in detail below.

It is advantageous also to remove other unsaturated byproducts which can be present in the R-245fa reaction product, including, for example, R-1223xd, R-1224zb, R-1224xe, R-1233xf, and the like. By way of specific example, chlorotetrafluoropropene (R-1224), including the various isomers thereof, has a boiling point which is similar to the boiling point of R-1233zd and is present as a by-product in the R-245fa reaction product in amounts like those of R-1233zd. Pursuant to the present invention, the amounts of such by-products can be reduced also to values corresponding to the reduced amounts of R-1233zd.

SUMMARY OF THE INVENTION 1-chloro-3,3,3-trifluoropropene (R-1233zd) is removed from a mixture consisting substantially of 1,1,1,3,3-pentafluoropropane (R-245fa) and containing up to about 20,000 wt. ppm R-1233zd by contacting the R-245fa mixture with 1–5 mols of chlorine for each mol of R-1233zd in the presence of ultraviolet light having a wavelength between about 300 to 400 nm which provides at least 0.02 watts-hour/kg of the mixture, preferably 0.02 to 2.0 watts-hour/kg. The R-1233zd can be reduced to below 10 wt. ppm or lower, as it is converted to 1,2,2-trichloro-3,3,3-trifluoropropane (R-233) or other propanes containing more chlorine such as R-223 or R-213, which have higher boiling points and can be easily separated from R-245fa. Other unsaturated compounds, such as R-1233xd, R-1224zb, R-1224xe, and R-1233xf, are also removed by chlorination to other derivatives which can be separated, for example by distillation. The temperature and pressure used may be adjusted to provide R-245fa in either the vapor or liquid phase, the vapor phase being preferred.

An advantage of the photochlorination of the present invention is that it does not affect materially the desired R-245fa product. Thus, while a high proportion of the R-1233zd impurity is in effect removed by the photochlorination, a substantially high proportion of the R-245fa is maintained. For example, the photochlorination can be effected in a manner such that at least about 96 wt. %, preferably at least about 98 wt. %, of the starting amount of R-245fa is maintained in the mixture. This is indeed surprising when it is considered that the proportion of R-245fa in the starting mixture is high, for example, at least about 98 wt. %.

DETAILED DESCRIPTION OF THE INVENTION

R-245fa may be produced by the process of U.S. Ser. No. 08/099,676, beginning from chloroform and vinylidene chloride. The crude product will contain a variety of by-products. It is of particular importance to remove 1-chloro-3,3,3-trifluoropropene (R-1233zd) from the crude product. Preliminary separation of R245fa by distillation will leave about 300 to 20,000 wt. ppm of R-1233zd having a boiling point of 19.2° C. compared to 15.3° C. for R-245fa, the difference in boiling points making R-1233zd difficult to separate from R245fa. In the process of the invention, R-1233zd or other unsaturated compounds which may be present, e.g. R1233xd, R-1224zb, R-1224xe, R-1233xf, are reacted with chlorine to provide more highly chlorinated compounds which have a higher boiling point and can be readily separated from R-245fa.

As mentioned above, the photochlorination can be effected so that at least about 96% (based on weight amount) or more of the desired starting amount of R-245fa is maintained in the mixture, that is, not affected by the photochlorination.

Process Conditions

In the process, crude R-245fa containing about 300 to 20,000 wt. ppm of R-1233zd along with minor amounts of other by-products such as those mentioned above will be contacted with chlorine in the presence of ultraviolet light having a wavelength of about 300 to 400 nm. It should be understood that an ultraviolet lamp may have radiation outside this range also, but that photochlorination requires UV light within this range.

The ultraviolet light will have an intensity which provides an exposure greater than zero and at least about 0.02 watts-hour/kg of the R-245fa mixture, preferably 0.02 to 2.0 watts-hour/kg.

The ultraviolet light may be provided by arc lamps including mercury, argon, or xenon and filament lamps including tungsten and halogen.

Chlorine is introduced into the crude R-245fa stream at a rate sufficient to provide about 1 to 5 mols of chlorine for each mol of R-1233zd, preferably 1 to 1.5.

It has been found that increasing either the ratio of chlorine to R-1233zd ($Cl_2$/R-1233zd) or the ultraviolet light exposure improves the chlorination of R-1233zd. Generally, we have been able to reduce the R-1233zd to below 10 wt. ppm using a UV exposure above about 0.04 watts-hour/kg but with quite low ratios of $Cl_2$/R-1233zd. Conversely, much lower UV exposures can be used if higher $Cl_2$/R-1233zd ratios are used. The $Cl_2$/R-1233zd ratio and UV exposure may be adjusted to provide the desired set of conditions.

The temperature employed may vary but may be from about -50° C. to 200° C., preferably about 25° to 60° C.

The pressure selected will be a convenient value to suit the processing conditions for R-245fa and to assure that R-245fa is a liquid or vapor, as desired.

The UV radiation from a lamp ordinarily will be expressed as watts, which is a rate of delivering energy. For present purposes, it is considered more useful to express radiation as the quantity of energy delivered over a period of time, i.e. the "exposure," rather than as the rate. Thus, the exposure may be expressed as watts-hours, which is related to the number of photons of energy delivered and their wavelength and these, in turn, relate to the chlorination of unsaturated molecules such as R-1233zd. Since the exposure is the product of the rate of delivering energy (photons/time) and the time, it will be clear that either the rate or the time could be varied. However, for practical applications the rate and the time will have limits imposed by the need to carry out the desired photochlorination reaction within constraints of time and product yield. If a high rate or a long time is used, not only will R-1233zd be chlorinated to R-233 (or R-223 or R-213), but chlorine will react with other molecules, particularly with R-245fa to make 3-chloro-1,1,1,3,3-pentafluropropane (R-235fa). Alternatively, if a very low rate or a short time is used, then insufficient chlorination of R-1233zd would be expected. Increasing the ratio of chlorine to R-245fa will tend to increase the production of (R-235fa). Conditions which involve a U.V. exposure of about 1.5 to 5.0 watts-hour/kg of R-245fa and a $Cl_2$/R-1233zd ratio (mol) about 1 to about 50:1 will tend to result in increased production of R-235fa.

As illustrated in the examples, the photochrlorination can be effected in a batch process or a continuous process.

After the R-245fa-containing mixture has been photochlorinated, the chlorinated products may be separated from the R-245fa, for example, by distillation, since the boiling points are no longer close to that of R-245fa. For example, the boiling points of R-233 and other chlorinated propanes that are typically produced in the photochlorination are at least about 60 C° above the boiling point of R-245fa (15.3° C.). To exemplify, the boiling points of R233 isomers are 95 to 110° C. and the boiling points of R-223 and R-213 isomers are respectively 125 to 135° C. and 152 to 157° C. The boiling point of R-235fa is 38.4° C. (The boiling points referred to in this specification are at one atmosphere pressure.) Separation of the Cl-containing by-products can be effected readily by conventionally distillation. Any residual chlorine, HCl or HF may be separated by absorption of chlorine in aqueous caustic, by adsorption on carbon molecular sieves, or reaction with aqueous sodium sulfite or sodium thiosulfate.

EXAMPLE 1

Liquid phase purification of R-245fa

The photochlorination of R-245fa was carried out in a 125 mL pyrex pressure vessel equipped with a dip leg inlet and a pressure gauge. This vessel was chilled in ice water and 20.0 grams of impure R-245fa, containing 0.08% R-1233zd was condensed into it. Then, while still cold, a stream of chlorine gas was passed at 10 mL/min through this solution for exactly 52 seconds. We calculate according to the ideal gas law that this should correspond to $3.6 \times 10^{-4}$ moles of chlorine, or a 1:1 mole ratio with the R-1233zd impurity. The vessel was then allowed to warm to room temperature.

The reactor vessel was placed for 5 minutes at the focus of RPR-100 Rayonet reactor (Southern New England Ultraviolet Company) equipped with 16 RPR-3500 lamps having their peak intensity at a wavelength of 350 nm. Light below 300 nm was removed by the pyrex walls of the pressure vessel. Ferrioxalate actinometry was used to measure the radiation received (see *The Chemists Companion*, A. J. Gordon & R. A. Ford, Wiley Interscience (1972), pages 362–368). In this vessel under these conditions this procedure gave an incident light intensity of $1.317 \times 10^{-7}$ einstein/sec (0.0417 watts). (One einstein is an equal to a mol of photons.) A five minute exposure should therefore have supplied $3.95 \times 10^{-5}$ einsteins of light (0.039 watt-hour/kg).

After exposure, the vapor head of the pressure vessel was sampled by gas chromatography using a 3048 mm long× 3.175 mm diameter column of 1% SP1000 on 60–80 mesh Carbopack B (Supelco Inc.) packing operated at 45° C. for 3 minutes and then programmed to increase 8° C./min to 200° C. This stream contained 0.00335% R-1233zd, and 0.0793% R-235fa.

EXAMPLE 2

Vapor phase purification of R-245fa

The photochlorination of R-245fa was carried out in a 125-mL pyrex pressure vessel equipped with an inlet at the bottom and an outlet at the top. The reactor vessel was placed at the focus of RPR-100 Rayonet reactor (Southern New England Ultraviolet Company) equipped with 16 RPR-3500 lamps having their peak intensity at a wavelength of 350 nm. Light below 300 nm was removed by the pyrex walls of the vessel. The vessel was unmersed in a pyrex constant temperature bath held at 59° C. to ensure that the R-245fa remained in the vapor phase.

Two feed streams were passed through separate lengths of capillary tubing and then mixed and passed into the reactor at 5 psig (34.5 kPa gauge). The impure R-245fa contained 0.080% R-1233zd plus other impurities. One stream contained impure R-245fa while the second contained chlorine.

By blending the two streams the ratio of chlorine to R-1233zd was varied. The radiation exposure was calculated from the residence time and the light intensity and varied from 2 to 3.5 watts-hour/kg. After exposure to the ultraviolet light the product stream was analyzed by gas chromatography using the procedures of Example 1.

The results of the tests at lower ratios of ($Cl_2$/R-1233zd are given in Table 1. The compounds are designated as refrigerants (R) according to the commonly used system of the American Society of Refrigerating Engineers.

TABLE 1

Vapor Phase Photochlorination to Remove Olefinic Impurities

| R-245fa Flow (mL/min) | Chlorine Flow Rate (mL/min) | Estimated Chlorine/R-1233zd Molar Ratio | Conc. R-1233zd (%) | Conc. R-235fa (%) |
|---|---|---|---|---|
| Feed | — | — | 0.0800 | 0.00091 |
| 49 | 3.0 | 26.5 | 0.0080* | 1.232 |
| 49 | 5.7 | 48.0 | N.D. | 8.789 |
| 91 | 0.99 | 4.7 | 0.00319 | 2.554 |

*value suspect, R-1233zd concentration should have been low since R-235fa has been produced.

EXAMPLE 3

Effect on Chlorine Ratio on R-245fa Purity

A series of experiments were done using the same general procedure as that described in Example 1. However, for each experiment, the weight of R-245fa, and the amount of chlorine introduced was changed, so as to explore the effect of changing the ratio of these reactants. All samples were exposed to UV light as described in Example 1 for 1 minute. Then GC analysis was completed as described. The amounts of reagents and experimental results are shown in Table 2 below.

TABLE 2

Effect of Chlorine Ratio on Performance in Liquid Phase

| Weight R-245fa (g) | Chlorine Flow Rate (mL/min) | Chlorine Flow Time (sec) | Calculated Moles Chlorine (×10⁵) | Calculated $Cl_2$/R-1233zd Molar Ratio | Conc. of R-1233zd (%) | Conc. of R-235fa (%) |
|---|---|---|---|---|---|---|
| Feed | — | — | — | — | 1.04 | 0.0027 |
| 17.3 | 2.97 | 30 | 5.8 | 0.096 | 0.935 | N.D. |
| 21.5 | 10.33 | 30 | 20.3 | 0.27 | 0.54 | 0.01 |
| 9.5 | 10.32 | 24 | 16.2 | 0.495 | 0.40 | 0.191 |
| 8.20 | 10.34 | 32 | 21.6 | 0.76 | 0.017 | 1.85 |
| 11.8 | 10.34 | 60 | 40.6 | 1.00* | 0.829* | N.D.* |
| 23.7 | 10.33 | 160 | 108.1 | 1.22 | 0.0003 | 0.66 |
| 23.9 | 10.33 | 180 | 121.6 | 1.47 | N.D. | 4.05 |

*Air contamination suspected, which will prevent the photochlorination from occurring.

It can be seen that the concentration of R-1233zd decreases as the ratio of $Cl_2$/R-1233zd is increased. Theoretically one mol of chlorine can react with on mol of R-1233zd to yield one mol of R-233. The results show that a ratio of about 1.47/1 essentially all of the R-1233zd has been converted within the limits of analytical precision. The product of chlorination of R-245fa, i.e., R-235fa is seen to appear at a ratio of about 0.5/1. Therefore, the preferred ratio of $Cl_2$/R-1233zd is considered to be about 1.0/1 to 1.3/1 when only the removal of R-1233zd is desired.

EXAMPLE 4

Effect of Light Intensity on Photochlorination Performance

A series of experiments were done using the same general procedure as that described in Example 1. However, for each experiment, the light intensity was varied by varying the number of light bulbs used in the Rayonet reactor. Ferrioxalate actinometry was ued to measure the radiation received (see *The Chemists Companion*, A. J. Gordon & R. A. Ford, Wiley Interscience (1972), pages 362–368). All samples were exposed to UV light as described in Example 1 for 1 minute. Then GC analysis was completed as described. The amounts of reagents and experimental results are shown in Table 3 below.

TABLE 3

Effect of Light Intensity of Performance in Liquid Phase

| Weight R-245fa (g) | Chlorine Flow Rate (mL/min) | Chlorine Flow Time (sec) | Calculated Moles Chlorine (×10⁵) | Calculated $Cl_2$/R-1233zd Molar Ratio | Light Intensity Einsteins/sec × 10⁷ | Conc. of R-1233zd (%) | Conc. of R-235fa (%) |
|---|---|---|---|---|---|---|---|
| Feed | — | — | — | — | — | 1.04 | 0.0027 |
| 23.1 | 10.32 | 118 | 79.7 | 1.0 | 1.317 | 0.00574 | 3.02 |
| 19.3 | 10.32 | 99 | 66.6 | 1.0 | 1.181 | 0.0764* | 0.799* |
| 15.5 | 10.32 | 79 | 55.4 | 1.0 | 0.866 | 0.0112 | 2.678 |
| 14.8 | 51.1 | 76 | 51.1 | 1.0 | 0.410 | 0.1116 | 2.047 |

*Air contamination suspected

This set of experiments shows that, as might be expected for a light-driven reaction, more light results in higher conversions. This effect is evident in both in the conversion of R-1233zd to more highly chlorinated species and the conversion of R-245fa to R-235fa. The experimental results can also be used to measure the quantum yield of the process, which is defined as the ratio of the rate of chlorination (in moles/second) and the intensity of light incident on the sample (in einsteins/second). Since an einstein is a mole of photons, this quantity is unitless. We calculate that the quantum yield measured in this set of experiments is roughly 100.

The next example shows the results of photochlorination on impurities in a R-245fa mixture under gas phase flow conditions,

EXAMPLE 5

Impure R-245fa was contacted with chlorine gas in a pyrex flow-through photochemical reactor centered in the focus of a Rayonet photoreactor. The temperature of this reactor was 50° C. and the pressure was 3 to 10 psig. The flow rates of R-245fa and chlorine were varied, as shown in Table 4 below, in order to evaluate the effects of the use of various ratios of chlorine to R-245fa and various residence times in the reactor. The feed composition is also shown in Table 4. The effluent gas from the photochemical reactor was analyzed by gas chromatography to determine the effects of reaction on the concentrations of impurities. It was observed that, at appropriate ratios of chlorine to R-245fa, the chlorine destroyed selectively the olefinic impurities, despite their low concentration, without co-generation of large amounts of R-235fa.

TABLE 4

| | | | | |
|---|---|---|---|---|
| R-245fa flow, mL/min | 252 | 100.8 | 252 | 100.8 |
| Cl$_2$ flow, mL/min | 0.97 | 0.39 | 1.88 | 0.75 |
| Cl$_2$/Tot. Olefins (mole ratio) | 1.29 | 1.29 | 2.49 | 2.49 |
| Exposure (W hr/kg) | 4.62 | 11.55 | 4.62 | 11.55 |
| | Feed, Concentrations in Area Percent | | Reaction Products, Concentrations in Area Per Cent | |
| R-1234 isomer | 0.02615 | 0.02386 | 0.02904 | 0.01135 | 0.011 |
| R-245fa | 98.36278 | 98.83418 | 98.80373 | 97.69573 | 98.53598 |
| R-1234 isomer | 0.01664 | 0.006345 | 0.009705 | 0.001315 | 0.00366 |
| R-1224 | 0.09259 | 0.040025 | 0.06058 | 0.00721 | 0.004685 |
| R-1233zd | 0.11411 | 0.057405 | 0.088725 | 0.011415 | 0.009815 |
| R-235fa | 0.193645 | 0.424145 | 0.21385 | 1.534255 | 0.56157 |
| R-1224 isomer | 0.01811 | 0.00729 | 0.01114 | 0.00149 | 0.000955 |
| R-374 isomer | 0.25609 | 0.211935 | 0.248785 | 0.21643 | 0.216285 |
| R-1214 isomer | 0.01185 | 0.003715 | 0.00491 | 0.0026 | 0.00094 |
| R-1214 isomer | 0.015955 | 0.009845 | 0.011285 | 0.01167 | 0.01026 |
| R-1223xd isomer | 0.014695 | 0.01211 | 0.01328 | 0.009225 | 0.024605 |
| R-1223xd isomer | 0.003085 | 0.00199 | 0.002775 | 0.002285 | 0.00275 |
| R-234 isomer | 0.07257 | 0.050825 | 0.05632 | 0.07573 | 0.0641 |
| R-233da | 0.30806 | 0.106175 | 0.137075 | 0.151225 | 0.143535 |
| Total Olefins | 0.313185 | 0.162585 | 0.23144 | 0.05856 | 0.06867 |
| Saturated Impurities | 0.757795 | 0.742255 | 0.59971 | 1.90191 | 0.92139 |

Review of information in Table 4 above shows that the photochlorination is extremely effective in reducing the amounts of undesired olefinic impurities without reducing to any significant extent the amount of R-245fa.

What is claimed is:

1. A process for removing 1-chloro-3,3,3-trifluoropropene (R-1233zd) or other olefinic impurities from 1,1,1,3,3-pentafluoropropane (R-245fa) by photochlorination comprising (a) contacting a mixture consisting substantially of a predetermined weight amount of R-245fa and up to about 20,000 wt. ppm R-1233zd with about 1–5 mols of chlorine for each mol of R-1233zd or other olefins in the presence of ultraviolet light having wavelengths between about 300 and 400 nm providing an exposure greater than zero and at least 0.02 watt-hour/kg of said mixture, said photochlorination being effective to reduce the concentration in the mixture of R-1233zd or other olefins to less than 100 ppm (wt.) by converting said R-1233zd to trichloro-trifluoropropane (R-233) or other propane which contains greater amounts of chlorine, as at least about 96% of said predetermined weight amount of R-245fa is maintained in the mixture; and (b) separating the R-233 or other propane formed in (a) from R-245fa.

2. A process according to claim 1 wherein the boiling point of said R-233 or other propane is at least about 60 C° above the boiling point of said R-245fa and separating the R-245fa and the R-233 or other propane by distillation.

3. The process of claim 1 effected as a batch process.

4. The process of claim 1 wherein said ultraviolet light provides an exposure of about 0.02 to 2 watts-hour/kg of said mixture.

5. The process of claim 1 wherein about 1 to 1.5 mols of chlorine are present for each mol of R-1233zd.

6. The process of claim 1 wherein the contacting of (a) is carried out at a temperature and a pressure sufficient to assure that R-245fa is liquid.

7. The process of claim 1 wherein the contacting of (a) is carried out at a temperature and a pressure at which R-245fa is vapor.

8. The process of claim 1 wherein the temperature is in the range of about −50° C. to 200° C.

9. The process of claim 8 wherein the temperature is in the range of about 25° C. to 60° C.

10. The process of claim 1 wherein the separation of (b) is carried out by distillation.

11. The process of claim 1 wherein said other olefinic impurities comprise at least one member of the group consisting of R-1223xd, R-1224zb, R-1224xe, and R-1233xf.

12. The process of claim 1 effected as a continuous process.

* * * * *